United States Patent [19]
Fraser et al.

[11] Patent Number: 4,760,851
[45] Date of Patent: Aug. 2, 1988

[54] 3-DIMENSIONAL DIGITIZER FOR SKELETAL ANALYSIS

[75] Inventors: Gregory A. Fraser, Dollard des Ormeaux; Simon Raab, Lorraine, both of Canada

[73] Assignee: Faro Medical Technologies Inc., Montreal, Canada

[21] Appl. No.: 846,244

[22] Filed: Mar. 31, 1986

[51] Int. Cl.$^4$ .............................................. A61B 5/10
[52] U.S. Cl. ..................................... 128/774; 128/781
[58] Field of Search ............... 128/774, 781, 782, 736; 33/511, 515

[56] References Cited

U.S. PATENT DOCUMENTS

| | | | |
|---|---|---|---|
| 2,324,672 | 7/1943 | Bierman et al. | 128/781 |
| 3,133,355 | 5/1964 | Gordon | 128/774 |
| 3,938,387 | 2/1976 | Flesch | 128/736 |
| 3,955,285 | 5/1976 | Moeckl | 33/515 |
| 4,365,638 | 12/1982 | Leveque et al. | 128/774 |
| 4,425,713 | 1/1984 | Rotella | 128/774 |
| 4,492,236 | 1/1985 | Pile | 128/781 |
| 4,549,555 | 10/1985 | Fraser et al. | 128/782 |
| 4,571,834 | 2/1986 | Fraser et al. | 128/782 |
| 4,586,515 | 5/1986 | Berger | 128/782 |
| 4,603,486 | 8/1986 | Moroney et al. | 128/781 |

FOREIGN PATENT DOCUMENTS

| | | | |
|---|---|---|---|
| 0160211 | 5/1983 | Fed. Rep. of Germany | 128/774 |
| 43487 | 1/1960 | Poland | 128/774 |
| 0760954 | 9/1980 | U.S.S.R. | 128/774 |

Primary Examiner—Max Hindenburg
Attorney, Agent, or Firm—Fishman, Dionne & Cantor

[57] ABSTRACT

A method of performing 3-dimensional skeletal analysis on a patient using an apparatus which includes a digitizer, the digitizer being adapted to accept either a scanning digitizer tip or a point digitizer tip, includes the steps of placing the patient in a variety of positions relevant to musculoskeletal problems and performing a series of rolling scans, with the scanning digitizer tip and single point landmark digitizations of musculoskeletal landmarks, with the point digitizer tip to obtain 3-dimensional skeletal data. The data is analyzed in order to provide clinically relevant 3-dimensional information relating to musculoskeletal quantities and imbalances. An apparatus for carrying out the method includes an upright column support and a retractable column support movable along the support column for supporting the patient. A digitizer measures the position of a point, or a group of points, on the patient's body in 3-dimensional space. The digitizer includes a plurality of rotatable transducers and a plurality of link members linking the rotatable transducers. The digitizer is connected at one end to the support column and has a free end. The free end of the digitizer is adapted to accept a digitizer tip. The apparatus also includes a computer and the output of the digitizer is connected to the computer whereby to provide data to the computer for computing the position of the point or group of points on the patient's body in 3-dimensional space.

12 Claims, 2 Drawing Sheets

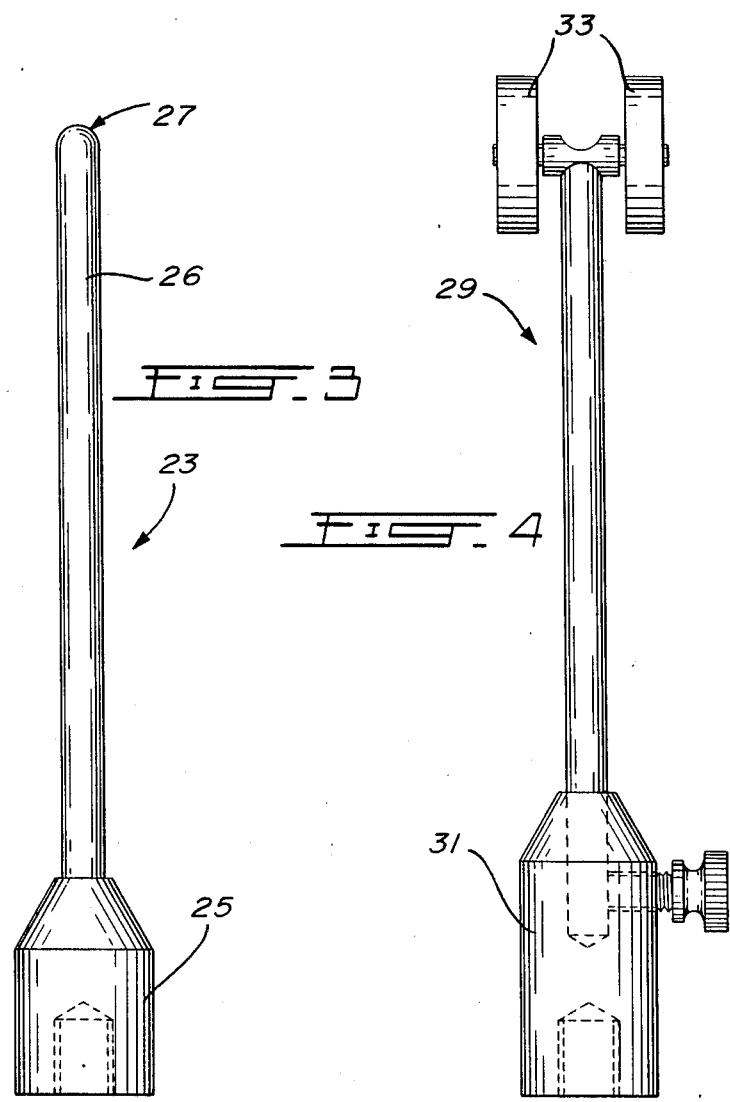

3-DIMENSIONAL DIGITIZER FOR SKELETAL ANALYSIS

BACKGROUND OF INVENTION

1. Field of the Invention

The invention relates to an apparatus for 3-dimensional skeletal analysis. More specifically, the invention relates to such an apparatus which includes a 3-dimensional digitizer.

The invention also relates to methods for analysis of skeletal balance for purposes of diagnoses, treatment and rehabilitation.

2. Description of Prior Art

Apparatus for skeletal analysis are known in the art as illustrated in, for example, U.S. Pat. No. 2,324,672, Bierman et al, July 20, 1943, U.S. Pat. No. 2,532,915, Horner, Dec. 5, 1950, U.S. Pat. No. 4,036,213, Gregory, July 19, 1977 and U.S. Pat. No. 4,492,236, Pile, Jan. 8, 1985.

The '672 patent uses an upstanding support column which measures the curvature of the spine with a bendable member 25 which traces the curvature of the spine as shown in FIGS. 3 and 5 of the patent. The apparatus is limited in that it measures only one parameter, namely, curvature of the spine, and it does so only along the single line of the spine. Finally, the apparatus in the '672 patent appears to provide only a two-dimensional measurement.

The '915 patent uses an audible sound transmitter and audio receivers 10 and 11 disposed on either side of the vertebrae to determine whether the spine is running along a straight vertical line or whether it is bent out of shape. The patent uses a radar principle for this purpose. Again, the apparatus is restricted to a single parameter measurement, that is, measurement of curvature of the spine. In addition, it also provides only a two-dimensional measurement.

The '213 patent, which also uses a vertically extending column, carries a sliding probe 52 to determine the position of vertebrae in a human patient. The positions of the vertebrae are determined relative to one another. This apparatus also does not permit three-dimensional scans.

The '236 patent relates to an apparatus for balancing skeletal alignment. The apparatus requires a very complex alignment procedure.

SUMMARY OF INVENTION

It is therefore an object of the invention to provide an apparatus which overcomes the disadvantages of the prior art.

It is a further object of the invention to provide an apparatus which permits 3-dimensional measurements.

It is a still further object of the invention to provide methods for analysis of skeletal balance using the inventive apparatus.

In accordance with the invention, there is provided a method of performing 3-dimensional skeletal analysis on a patient using an apparatus which includes digitizer means, the digitizer means being adapted to accept either a scanning digitizer tip or a point digitizer tip. The method includes the steps of placing the patient in a variety of positions relevant to musculoskeletal problems and performing a series of rolling scans, with the scanning digitizer tip, and single point landmark digitizations of musculoskeletal landmarks, with the point digitizer tip to obtain 3-dimensional skeletal data. The data is analyzed in order to provide clincially relevant 3-dimensional information relating to musculoskeletal quantities and imbalances.

From a different aspect, there is provided an apparatus for performing 3-dimensional skeletal analysis on a patient. The apparatus includes an upright column support and a retractable column support means movable along the support column for supporting the patient. Digitizer means measure the position of a point, or a group of points, on the patient's body in 3-dimensional space. The digitizer means include a plurality of rotatable transducers and a plurality of link members linking the rotatable transducers. The digitizer means are connected at one end to the support column and having a free end. The free end of the digitizer means is adapted to accept a digitizer tip. The apparatus also includes computer means and means connecting the output of the digitizer means to the computer means whereby to provide data to the computer means for computing the position of the point or group of points on the patient's body in 3-dimensional space.

BRIEF DESCRIPTION OF DRAWINGS

The invention will be better understood by an examination of the following description, together with the accompanying drawings, in which:

FIG. 2 is a top view with a patient shown in a different position than in FIG. 1;

FIG. 3 illustrates a single point digitizer; and

FIG. 4 illustrates a rolling wheel digitizer.

DESCRIPTION OF PREFERRED EMBODIMENTS

Figure 1:
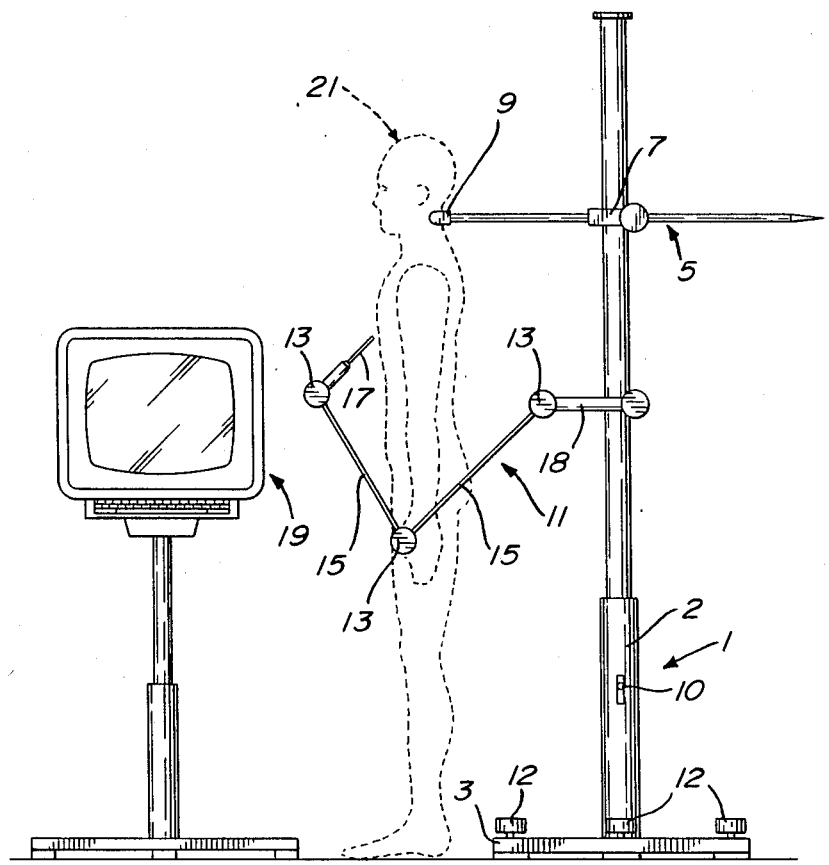
FIG. 1 is a side view of the apparatus with a patient shown in standing position.

Referring to FIG. 1, the apparatus includes a support column 1 insertable into floor stand 2 which is, in turn, mounted on a base 3. A retractable support 5 is mounted for sliding on the support column by a sliding clamping block 7. One end of the retractable support has a curved support 9 which can be rotated and consists of a curved padded body so that it can be aligned with various portions of the body depending on the application required. The retractable support 5 eliminates the general swaying that occurs during the postural analysis and enhances the ultimate accuracy of the measurement. The support can travel vertically along the support column through appropriate manipulation of the sliding clamping block.

Included on the floor stand is a means 10 for setting the vertical column in its correct vertical orientation, i.e., a spirit level. The vertical orientation is adjustable by adjustment means 12 on the base 3.

Figure 1A:
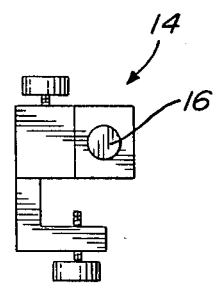
FIG. 1A is a level adjusting clamp.

The vertical column is removable from the floor stand 2 for mounting on a tree stand or on a table edge. Level adjusting clamp 14 (see FIG. 1A) including spirit level 16, can be used to mount the vertical column on a table edge.

The apparatus also includes a 3-dimensional digitizer 11 which includes a plurality of rotational transducers 13 linked together by link members 15. A digitizer tip 17 is placed at the free end of the 3-dimensional digitizer. The 3-dimensional digitizer is a six-degree of freedom device capable of measuring the position of a point or group of points in 3-dimensional space through the use of the link members connecting the rotational transducers, that is, transducers capable of measuring rotation. The 3-dimensional digitizer is more fully described in my U.S. Pat. No. 4,549,555, the contents of which are incorporated herein by reference.

The digitizer is also mounted on the support column 1 by means of a sliding clamp block 18 whereby the digitizer can be moved vertically up and down along the support column. Output from the digitizer is fed to a microcomputer 19. A program for driving the microcomputer is also described in my U.S. Pat. No. 4,549,555.

A variety of digitizer tips are available for various digitization requirements as illustrated in FIGS. 3 and 4. FIG. 3 illustrates a single point digitizer tip at 23. The digitizer tip includes a mounting block 25, by which the digitizer tip is mounted on the 3-dimensional digitizer. Extending from the mounting block is a wand-like member 26. The free end 27 of the member 26 consists of a round tip of uniform diameter which is used to isolate the landmarks.

FIG. 4 illustrates a rolling wheel digitizer tip 29 which is mounted on the 3-dimensional digitizer by mounting block 31. It includes two rolling wheels 33. The rolling digitizer is mounted on the mounting block by frictional mounting so that the direction of rotation and the attitude of the rolling wheels can be adjusted. This tip is used for continuous scanning of points for the purpose of establishing contours of, for example, the spine and rib cage.

In operation, the patient 23 stands close to the vertical support with his side (as in FIG. 2) or back (as in FIG. 1) towards the device in order to permit access to both the front and the back of the patient by the linkage system of the 3-dimensional digitizer 11.

When the information from the 3-dimensional digitizer 11 is fed to the microcomputer 19, the data from the 3-dimensional digitizer is analyzed and is represented in a 3-dimensional co-ordinate system or in 3-dimensional co-ordinate systems for the purposes of performing clinical analysis.

The clinical technician may be prompted by the microcomputer through the use of the voice synthesizer which instructs the technician to place the digitizer tips on various skeletal landmarks in order to provide the device with proper co-ordinates to generate a skeletal balance analysis. The software for the microcomputer is menu-driven and will provide a variety of analyses relating to various physiological problems.

Data attained subsequent to the automatic prompts is then analysed by the microcomputer to provide the planes and angles of rotation, radii of curvature and variety of lengths required to determine the degree of structural imbalance of the patient.

The 3-dimensional digitizer has been designed to permit the use of a sterile sleeve which allows the device to be used in a surgical environment. For this purpose, the digitizer tips are removable and sterilizable using conventional auto claving techniques. The small foot print and portable microcomputer provide an ideal structure for the application in an already cramped surgical environment. In this particular application software routines are chosen from the menu which provides assistance in the orientation of total joint replacement prostheses as well as other varied 3-dimensional directional requirements of advanced orthopedic surgery, among others.

In accordance with the invention, the following methods are used, with the inventive apparatus, for skeletal analysis and balancing:

SCOLIOTIC SCANNING

In order to permit rapid accurate assessment of scoliosis in a school or clinic environment and by a lay person or school nurse, a series of progressive screening go/no go high-speed tests are provided. The series of tests are of increasing sophistication and detail ultimately resulting in an accurate referral report and comprise the following tests:
1. Rib hump scan
2. Vertebral scan
3. Lower extremity measurement.

Minimum requirements (deviations from the norm) must be reached at each stage in order to proceed to the next stage. Thus, if the mininum requirements or deviations are not reached in the rib hump scan, then it can be assumed that the patient is not afflicted by scoliosis, so that the remainder of the tests need not be performed. If the patient shows signs of scoliosis after all three tests, a print-out can be provided for the physician of referral.

1. For the rib hump scan the patient is bent forward at the hips by approximately 90° and three horizontal scans are performed. These scans would be performed with the rolling digitizer illustrated in FIG. 4. The horizontal rolling scans would be performed at the level of the center of the thoracic spine, then at the level of the thoracolumbar spine, and finally at the center of the lumbar spine. The scans provide a vertical profile of the trunk. The analysis involves the joining of the points of maximum deformity on the medial and lateral side in order to measure the angle of that line with the horizontal and therefore an angle of trunk rotation. A minimum of five degrees of trunk rotation at any level results in a recommendation of referral and the continuation to the next level of testing.

2. The vertebral scan is performed with the patient in the upright position. Once again, the rolling digitizer of FIG. 4 is used. The scan is started on the base of the skull and proceeds to the lumbosacral joint. Graphic output is provided in the final report with only Cobb angles presented for the neutral upright position. A Cobb angle of greater than twenty degrees is considered positive and leads to the next test.

3. The lower extremity measurement is also conducted with the patient in the upright position. In these measurements, the single point tip digitizer 23 of FIG. 3 is used. A number of isolated boney landmarks are digitized in order to quantify lower extremity contributions to the condition. These include pelvic rotation in two planes, leg length and apparent leg length in the upright position, digitization of the anterior and posterior superior illiac crests and of the malleoli.

GENERALIZED MEASUREMENT PROCEDURES

The generalized measurement procedures are used for documentation of scoliotic development principally used in the evaluation of treatment and rehabilitation. They consist of the following:
1. 3-D Back profile
2. Vertebral curvature analysis.
3. Lower extremity alignment.

1. The 3-D back profile is performed in the upright position and consists of a series of horizontal scans, usually ten, two-wheeled with digitizer 29, from the base of the cervical spine to the lumbosacral joints. The computer determines the vertical position of the next horizontal scan and informs the user of correct positioning. Topographical views are created including back, side and top views, providing topological data along three vertical lines along the vertebrae and along two lines approximately four inches right and left of this line and parallel to it. The highest point on any slice is indicated and the millimeters deviation from a standard upright line connecting the lumbosacral joint and the base of the skull is presented.

2. The vertebral curvature analysis is an analysis of the curvature of the spine and is made in three modes: upright, right leaning and left leaning. The intention of this measurement is to ascertain regions of the spine which remain flexible and those that have locked into a specific curvature. The two-wheeled digitizer tip 29 is used in this analysis and is tracked from the base of the skull to the lumbosacral joint in each of the three positions. The computer uses standard anatomical proportions to specify thoracic, thoracolumbar and lumbar regions. A two view graphic output is presented showing the Cobb angle for each of the three positions as well as providing assessments in millimeters of radii of curvature of kyphosis and lordosis.

3. A series of digitizations and scans are performed with two-wheeled digitizer tip 29, and with the patient in the upright position, from the pelvis down to the malleoli in order to determine the relative parameters such as leg length, physiological varus and valgus as well as other parameters which may affect upper body posture.

POSTURAL ANALYSIS

This group of routines is designed to permit the generalized assessment of postural faults for both the entire body and various important segments which contribute to the overall postural alignment. Rolling point scans are performed to determine general body form and posture followed by a series of landmark digitizations to establish plumb line alignment. The routines comprise the following:

1. Horizontal scans.
2. Vertical scans.
3. Specific landmark digitizations.

1. Three horizontal scans are taken as follows:
   a. At the level of T1 to the top of the thoracic vertebrae.
   b. Mid thoracic spine, approximately T7 to T8.
   c. At the level of L1 to the top of the lumbar spine.
  The two-wheel digitizer tip 29 is used for these routines.

2. The two-wheel digitizer tip 29 is also used in performing five vertical scans as follows:
   a. Inside and along the right and left legs.
   b. Outside right and left sides extending from under the earlobe to the lateral malleoli.
   c. Posterior base of the skull down to the lumbosacral joint.
   d. Four inches to the right and left of the last scan (3).
   e. Anterior and posterior of both legs comprised of a line joining the anterior superior pelvic crest to the toes, and the posterior gluteal crease to the base of the heel.

3. With the patient in the upright position, and using the single point digitizer 23 of FIG. 3, the following landmark digitization measurements are taken:
   a. Medial and lateral malleoli
   b. Medial and lateral knee joint line.
   c. Posterior pelvic crest right and left.
   d. Anterior superior illiac crests, right and left.
   e. Right and left greater trochanter.
   f. Right and left earlobe.
   g. Medial and lateral edge of patella on right and left leg.
   h. Chin center and superior aspect of the bridge of the nose.
   i. Inside and outside edge of the foot/floor contact, right and left.

The postural analysis routines provide a tabular and graphical output describing plumb line segmental alignment, radii of kyphosis and lordosis, leg length, etc. This output can be used for the assessment of general postural progress and treatment as well as diagnosis and treatment selection.

In the preceding discussion, the digitizer tips were described as instruments for measuring position parameters. However, the digitizer tips can be modified to measure other parameters, for example, temperature or stiffness, as well.

For example, the wand-like member 26 of the digitizer tip 23 in FIG. 3 can comprise a temperature probe having a temperature transducer at the free end 27 thereof. Using such a temperature probe, it is then possible to scan temperature gradients in a 3-dimensional space and to map them graphically. This capability has applications in many areas other than medicine, however, in the present application, the capability can be used to measure localized temperature variations about a sore joint to thereby determine the exact site of the injury.

The wand-like member 26 can also comprise a stiffness probe. In this case, the free end 27 of the wand-like member 26 would comprise a force transducer to give the digitizer tip the capability of measuring stiffness in a variety of locations in 3-dimensional space. For example, the application of a force to various vertebra of the spine using the force transducer gives the capability of determining the stiffness, that is, the deformation with force, at various locations of the spine to thereby produce a 3-dimensional picture of spine stiffness.

Although only temperature and stiffness probes have been above-discussed, it will be appreciated that, by placement of different transducers, various parameters can be assessed within a 3-dimensional space and thereby graphically represented for analysis. As will be clear to one skilled in the art, the transducers will be connected to the microprocessor by leads extending through the probe and through the digitizer elements. Such electrical connections are well known to one skilled in the art and require no further description at this time.

The electrical signals carried by the leads from the transducers are analyzed in conjunction with the electrogoniometer signals by the microprocessor and processed using appropriate software. In this regard, the only additional software which would have to be provided would be software for transforming the electrical signals to parameter values (i.e., transforming electrical signals to temperature or stiffness values). Software is already provided for determining the position in 3-dimensional space of the probe tips.

Although specific embodiments have been above-described, this was for the purpose of illustrating, but not limiting, the invention. Various modifications, which will come readily to the mind of one skilled in the art, are within the scope of the invention as defined in the appended claims.

We claim:

1. A method of performing 3-dimensional skeletal analysis on a patient using an apparatus which includes digitizer means, said digitizer means comprising a plurality of rotatable transducers, a plurality of link members linking said rotatable transducers, and a digitizer tip having a free end, said digitizer means accepting either a scanning digitizer tip or a point digitizer tip, said scanning tip comprising means at the free end thereof for performing scans, said point digitizer tip comprising a point at the free end thereof for performing single point landmark digitizations, said method comprising the steps of:

(A) placing the patient in a variety of positions relevant to musculoskeletal problems, the position of said patient being changed, as required, between the performance of the steps as recited in paragraph (B) below;

(B) performing a series of scans, with said scanning digitizer tip, by moving said scanning digitizer tip along lines of interest on the surface of said patient's body, and performing single point landmark digitizations of musculoskeletal landmarks, with said point digitizer tip, by moving said point of said point digitizer tip to points of interest on the surface of said patient's body, to obtain 3-dimensional skeletal data;

(C) analyzing said data in order to provide clinically relevant 3-dimensional information relating to musculoskeletal quantitites and imbalances.

2. A method as defined in claim 1 wherein said apparatus comprises computer means;

wherein said data is analyzed using said computer means.

3. A method as defined in claim 2 wherein said variety of positions comprises a first position, a second position and a third position;

and wherein said series of scans comprises a first rolling scan and a second scan;

and comprising the steps of:

1. placing said patient in said first position and performing said first series of scans on the patient using said scanning digitizer tip;

2. placing the patient in said second position and performing said second series of scans using said scanning digitizer tip; and 3. placing said patient in said third position and performing said series of single point landmark digitizations using said point digitizer tip.

4. A method as defined in claim 3 for performing scoliotic scanning and comprising the steps of:

1. performing a rib hump scan wherein, in said first position, said patient is bent forward at the hips by approximately 90°, and said first series of scans comprises three horizontal scans at the (1) level of the center of the thoracic spine, (2) at the level of the thoracolumbar spine, and (3) at the center of the lumbar spine;

2. performing a vertebral scan wherein, in said second position, said patient is in an upright position, and wherein said second series of scans comprises a scan starting on the base of the skull and proceeding to the lumbosacral joint whereby to provide only Cobb angles presented for the neutral upright position; and 3. performing a lower extremity measurement wherein, in said third position, said patient is in the upright position and wherein said series of single point landmark digitizations comprise a number of isolated boney landmarks digitized in order to quantify lower extremity contributions to the conditions; said isolated boney landmarks comprising pelvic rotation in two planes, leg length and apparent leg length in the upright position, and digitization of the anterior and posterior superior illiac crests and the malleoli.

5. A method as defined in claim 3 for performing generalized measurement procedures and comprising:

1. performing a 3-dimensional back profile wherein, in said first position, said patient is in the upright position and wherein said first series of scans comprises a series of up to ten horizontal scans from the base of the cervical spine to the lumbosacral joints;

2. performing vertebral curvature analysis wherein said second position comprises three modes: upright, right leaning and left leaning, and wherein said second series of scans comprises a scan from the base of the skull to the lumbosacral joint in each of the three positions;

3. performing a lower extremity alignment wherein, in said third position, said patient is in an upright position, and wherein said series of single point landmark digitizations comprise digitizations from the pelvis down to the malleoli, and further including scans from the pelvis down to the malleoli, in order to determine the relative parameter such as leg length, physiological varus and valgus, as well as other parameters which may affect upper body posture.

6. A method as defined in claim 3 for performing postural analysis:

1. performing horizontal scans wherein, in said first position, said patient is in an upright position, and said series of scans comprises:
   a. at the level of T1 to the top of the thoracic vertebrae;
   b. mid thoracic spine, approximately T7 to T8;
   c. at the level of L1 to the top of the lumbar spine;

2. performing vertical scans wherein, in said second position, said patient is in an upright position, and wherein said second series of scans comprises:
   a. inside and along the right and left legs;
   b. outside right and left sides extending from under the earlobe to the lateral malleoli;
   c. posterior base of the skull down to the lumbosacral joint;
   d. four inches to the right and left of the last scan (3);
   e. anterior and posterior of both legs comprised of a line joining the anterior superior pelvic crest to the toes, and the posterior gluteal crease to the base of the heel;

3. performing specific landmark digitizations wherein, in said third position, said patient is in an upright position, and wherein said series of single point landmark digitizations comprises:
   a. medial and lateral malleoli;
   b. medial and lateral knee joint line;
   c. posterior pelvic crest right and left;
   d. anterior and superior illiac crests, right and left;
   e. right and left greater trochanter;
   f. right and left earlobe;

g. medial and lateral edge of patella on right and left leg;

h. chin center and superior aspect of the bridge of the nose;

i. inside and outside edge of the foot/floor contact, right and left;

whereby to provide a tabular and graphical output describing plumb line segmental alignment, radii of kyphosis and lordosis and leg length.

7. A method as defined in claim 1 wherein said means at the free end thereof for performing scans comprises rolling means;

the step of moving said scanning digitizer comprising rolling said rolling means of said scanning digitizer tip along said lines of interest on the surface of said patient's body.

8. A method as defined in claim 7 wherein said apparatus comprises computer means;

wherein said data is analyzed using said computer means.

9. A method as defined in claim 8 wherein said variety of positions comprises a first position, a second position and a third position;

and wherein said series of rolling scans comprises a first rolling scan and a second rolling scan;

and comprising the steps of:

1. placing said patient in said first position and performing said first series of rolling scans on the patient using said scanning digitizer tip;

2. placing the patient in said second position and performing said second series of rolling scans using said scanning digitizer tip; and 3. placing said patient in said third position and performing said series of single point landmark digitizations using said point digitizer tip.

10. A method as defined in claim 9 for performing scoliotic scanning and comprising the steps of:

1. performing a rib hump scan wherein, in said first position, said patient is bent forward at the hips by approximately 90°, and said first series of rolling scans comprises three horizontal scans at (1) the level of the center of the thoracic spine, (2) the level of the thoracolumbar spine, and (3) the center of the lumbar spine;

2. performing a vertebral scan wherein, in said second position, said patient is in an upright position, and wherein said second series of rolling scans comprises a scan starting on the base of the skull and proceeding to the lumbosacral joint whereby to provide only Cobb angles presented for the neutral upright position; and 3. performing a lower extremity measurement wherein, in said third position, said patient is in the upright position and wherein said series of single point landmark digitizations comprise a number of isolated boney landmarks digitized in order to quantify lower extremity contributions to the conditions; said isolated boney landmarks comprising pelvic rotation in two planes, leg length and apparent leg length in the upright position, and digitization of the anterior and posterior superior illiac crests and the malleoli.

11. A method as defined in claim 9 for performing generalized measurement procedures and comprising:

1. performing a 3-dimensional back profile wherein, in said first position, said patient is in the upright position and wherein said first series of rolling scans comprises a series of up to ten horizontal scans from the base of the cervical spine to the lumbosacral joints;

2. performing vertebral curvature analysis wherein said second position comprises three modes: upright, right leaning and left leaning, and wherein said second series of scans comprises a scan from the base of the skull to the lumbosacral joint in each of the three positions;

3. performing a lower extremity alignment wherein, in said third position, said patient is in an upright position, and wherein said series of single point landmark digitizations comprise digitizations from the pelvis down to the malleoli, and further including rolling scans from the pelvis down to the malleoli, in order to determine the relative parameter such as leg length, physiological varus and valgus, as well as other parameters which may affect upper body posture.

12. A method as defined in claim 9 for performing postural analysis:

1. performing horizontal scans wherein, in said first position, said patient is in an upright position, and said series of rolling scans comprises:

a. at the level of T1 to the top of the thoracic vertebrae;

b. mid thoracic spine, approximately T7 to T8;

c. at the level of L1 to the top of the lumbar spine;

2. performing vertical scans wherein, in said second position, said patient is in an upright position, and wherein said second series of rolling scans comprises:

a. inside and along the right and left legs;

b. outside right and left sides extending from under the earlobe to the lateral malleoli;

c. posterior base of the skull down to the lumbosacral joint;

d. four inches to the right and left of the last scan (3);

e. anterior and posterior of both legs comprised of a line joining the anterior superior pelvic crest to the toes, and the posterior gluteal crase to the base of the heel;

3. performing specfic landmark digitizations wherein, in said third position, said patient is in an upright position, and wherein said series of single point landmark digitizations comprises:

a. medial and lateral malleoli;

b. medial and lateral knee joint line;

c. posterior pelvic crest right and left;

d. anterior and superior illiac crests, right and left, e. right and left greater trochanter;

f. right and left earlobe;

g. medial and lateral edge of patella on right and left leg;

h. chin center and superior aspect of the bridge of the nose;

i. inside and outside edge of the foot/floor contact, right and left;

whereby, to provide a tabular and graphical output describing plumb line segmental alignment, radii of kyphosis and lordosis and leg length.

* * * * *